(12) United States Patent
Harvey

(10) Patent No.: US 11,078,139 B1
(45) Date of Patent: Aug. 3, 2021

(54) CYCLOPENTADIENE FUELS

(71) Applicant: The United States of America as Represented by the Secretary of the Navy, Arlington, VA (US)

(72) Inventor: Benjamin G. Harvey, Ridgecrest, CA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 58 days.

(21) Appl. No.: 16/559,778

(22) Filed: Sep. 4, 2019

(51) Int. Cl.
| | |
|---|---|
| *C07C 29/145* | (2006.01) |
| *C07C 1/24* | (2006.01) |
| *C07C 2/52* | (2006.01) |
| *C07C 45/59* | (2006.01) |
| *C07C 5/22* | (2006.01) |
| *C07C 45/66* | (2006.01) |

(Continued)

(52) U.S. Cl.
CPC .......... *C07C 29/145* (2013.01); *C07C 1/24* (2013.01); *C07C 2/52* (2013.01); *C07C 5/2206* (2013.01); *C07C 7/04* (2013.01); *C07C 45/41* (2013.01); *C07C 45/59* (2013.01); *C07C 45/61* (2013.01); *C07C 45/66* (2013.01); *C07C 51/36* (2013.01); *C07C 51/42* (2013.01); *C07C 67/08* (2013.01); *C07C 2521/02* (2013.01); *C07C 2527/18* (2013.01); *C07C 2531/08* (2013.01)

(58) Field of Classification Search
CPC .......... C07C 29/145; C07C 1/24; C07C 2/52; C07C 5/22; C07C 45/59; C07C 45/66; C07C 51/36; C07C 67/08; C07C 45/41; C07C 51/42; C07C 45/61; C07C 7/04
See application file for complete search history.

(56) References Cited

U.S. PATENT DOCUMENTS

| | | | |
|---|---|---|---|
| 5,118,864 A | 6/1992 | Merger et al. | |
| 9,327,279 B2 * | 5/2016 | Harvey | C10G 65/043 |

(Continued)

FOREIGN PATENT DOCUMENTS

| | | |
|---|---|---|
| EP | 446759 | 9/1991 |
| WO | WO 2016077361 | 5/2016 |

OTHER PUBLICATIONS

Yanliang Yang et al., Conversion of furfural into cyclopentanone over Ni—Cu bimetllic catalysts, Green Chem, 2013, 15, 1932-1940.

(Continued)

*Primary Examiner* — Youngsul Jeong
(74) *Attorney, Agent, or Firm* — Naval Air Warfare Center Weapons Division; Matthew D. Pangallo; Stuart H. Nissim

(57) ABSTRACT

A method for making cyclopentadiene fuels comprising producing cyclopent-2-en-1-one or a mixture of cyclopent-2-en-1-one from a bio-based source. The cyclopent-2-en-1-one or the mixture of cyclopent-2-en-1-one is hydrogenated, thereby forming cyclopent-2-en-1-ol or a mixture of cyclopent-2-en-1-ol. The cyclopent-2-en-1-ol or the mixture of cyclopent-2-en-1-ol is dehydrated with a dehydrating agent, thereby forming cyclopentadiene or a mixture of cyclopentadiene. The cyclopentadiene or mixture of cyclopentadiene is converted to dicyclopentadiene or dihydrodicyclopentadiene. The dicyclopentadiene or dihydrodicyclopentadiene is hydrogenated, thereby forming tetrahydrodicyclopentadiene. The tetrahydrodicyclopentadiene is isomerized, thereby forming exo-tetrahydrodicyclopentadiene.

18 Claims, 6 Drawing Sheets

(51) Int. Cl.
    *C07C 51/36*      (2006.01)
    *C07C 67/08*      (2006.01)
    *C07C 45/41*      (2006.01)
    *C07C 51/42*      (2006.01)
    *C07C 45/61*      (2006.01)
    *C07C 7/04*      (2006.01)

(56) References Cited

U.S. PATENT DOCUMENTS

| | | | |
|---|---|---|---|
| 9,493,717 B2 * | 11/2016 | Harvey | C07C 4/10 |
| 9,963,652 B1 * | 5/2018 | Harvey | C07C 5/03 |
| 2004/0102655 A1 | 5/2004 | Liang et al. | |
| 2016/0145227 A1 | 5/2016 | Dugar et al. | |

OTHER PUBLICATIONS

Dezhang Ren et al., Production of 2,5-hexanedione and 3-methyl-2-cyclopenten-1-one from 5-hydromethylfurfural, Green Chem 2016, 18, 3075-3081.

Heather A. Meylemans et al., Solvent-Free Conversion of Linalool to methylcyclopentadiene dimers: A Route to Renewable High-Density Fuels, ChemSusChem, Feb. 2011, 4, 465-469.

Christopher W. Johnson et al., Enhancing muconic acid production from glucose and lignin-derived aromatic compounds via increased protocatechuate decarboxylase activity, Metabolic Engineering Communications, Dec. 2016, 3, 111-119.

* cited by examiner

CYCLOPENTADIENE FUELS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Fuel precursors can be chemically produced from petroleum and bio-based sources or obtained from naturally occurring crude oil sources. When producing fuel, the precursors are added to a distillation column with a temperature gradient to separate the various hydrocarbon molecules within the fuel precursor. The hydrocarbon molecules are separated by size and subjected to a specific treatment to produce a fuel for a specific application. For example, jet fuel may contain a mixture of hydrocarbons ranging from 5 to 16 carbon atoms in each molecule. These hydrocarbons are separated from the column after boiling and specifically treated to produce jet fuel. As a result, distilling a fuel precursor may produce a variety of fuels for different applications in a single distillation.

BRIEF DESCRIPTION OF THE DRAWINGS

Features and advantages of examples of the present disclosure will be apparent by reference to the following detailed description and drawings, in which like reference numerals correspond to similar, though perhaps not identical, components. Reference numerals or features having a previously described function may or may not be described in connection with other drawings in which they appear.

DETAILED DESCRIPTION

Traditionally, exo-tetrahydrodicyclopentadiene, which forms a majority of a Jet Propellant 10 (JP-10) fuel composition, is produced from dicyclopentadiene derived from either petroleum distillates or naphtha cracking. These methods do not utilize sustainable fuel precursors to produce JP-10 fuel. As a result, JP-10 production is reliant on petroleum products, including those generated by naphtha cracking methods, which are not selective for producing pure cyclopentadienes. Since the methods are not selective, additional steps are required to separate the cyclopentadienes from undesirable products, which makes traditional methods of producing JP-10 fuel expensive. Therefore, the production of JP-10 fuel is limited due to the cost of production.

In the disclosure herein, methods for making cyclopentadiene fuels (i.e., JP-10) are provided. The fuel can be produced from sustainable bio-based sources. As a result, cyclopentadiene fuel can be produced in greater quantities using a cheaper production method compared to producing the fuel using conventional methods. The increased availability and decreased price of JP-10 afforded by this process will allow for its use in a wider variety of vehicles and enhance the performance of aircraft. Furthermore, cyclopentadiene, primarily in the form of dicyclopentadiene, is used in a variety of other industries. Therefore, sustainable production will also have an impact on products that use dicyclopentadiene (e.g., unsaturated polyester resins, inks, adhesives, paints, etc.).

The method for making cyclopentadiene fuels (i.e., JP-10) herein includes producing cyclopent-2-en-1-one or a mixture of cyclopent-2-en-1-one from a bio-based source. Hydrogenating the cyclopent-2-en-1-one or the mixture of cyclopent-2-en-1-one, thereby forming cyclopent-2-en-1-ol or a mixture of cyclopent-2-en-1-ol. Dehydrating the cyclopent-2-en-1-ol or the mixture of cyclopent-2-en-1-ol with a dehydrating agent, thereby forming cyclopentadiene or a mixture of cyclopentadiene. Converting the cyclopentadiene or the mixture of cyclopentadiene to dicyclopentadiene. Hydrogenating the dicyclopentadiene, thereby forming tetrahydrodicyclopentadiene. Isomerizing the tetrahydrodicyclopentadiene, thereby forming exo-tetrahydrodicyclopentadiene.

Figure 1:
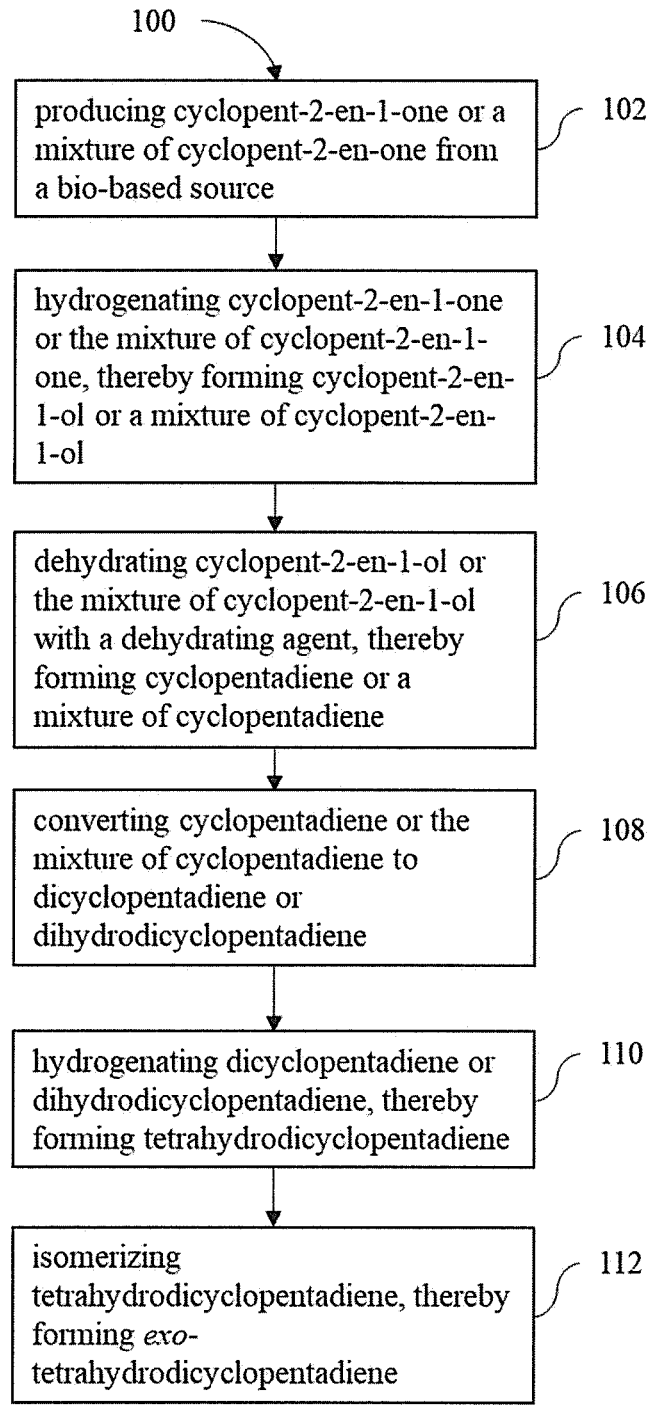
FIG. 1 is a flow diagram illustrating an example of a method of making cyclopentadiene fuels described herein.

Referring now to FIG. 1, step 102 for the method 100 of making cyclopentadiene fuel (JP-10) includes producing cyclopent-2-en-1-one or a mixture of cyclopent-2-en-1-one from a bio-based source. Cyclopent-2-en-1-one is a precursor molecule to produce exo-tetrahydrodicyclopentadiene, the majority of the JP-10 fuel composition. Producing cyclopent-2-en-1-one or a mixture of cyclopent-2-en-1-one from a bio-based source allows for sustainable production of JP-10 fuel rather than producing the fuel from petroleum based sources, which is costly and non-sustainable. There are multiple methods that can be used to produce the precursor molecule, cyclopent-2-en-1-one, from bio-based sources to subsequently produce JP-10 fuel. Some examples of these methods are described below.

Figure 2:
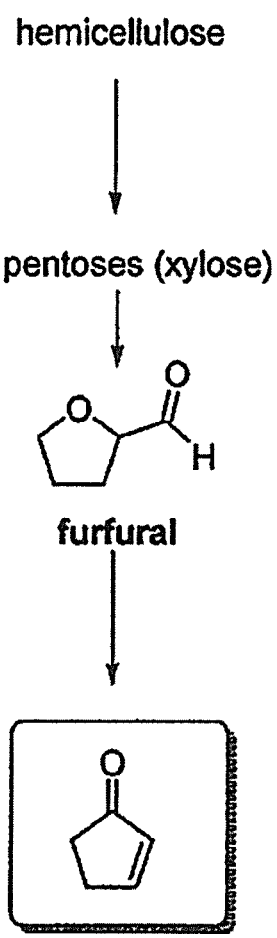
FIG. 2 is a scheme illustrating an example of a method of making cyclopent-2-en-1-one from hemicellulose.

In one example, shown in FIG. 2, cyclopent-2-en-1-one is produced from hemicellulose (e.g., wood chips, corn husks, etc.). Hemicellulose can be obtained from abundant, sustainable sources. Hemicellulose is used as the bio-based source to produce pentoses (e.g., xylose). Any known method for producing pentoses from hemicellulose can be used. For example, one method includes catalyzing the conversion of hemicellulose to pentoses with formic acid or a solid acid catalyst.

After obtaining pentoses, a two-step process can be used to produce furfural or furfuryl alcohol, which is then converted to 4-hydroxy-2-cyclopentenone or a combination of furfuryl alcohol and 4-hydroxy-2-cyclopentenone. First, a pentose (e.g., xylose) is converted to furfural or furfuryl alcohol using acid catalysts known in the art to catalyze the reaction. Second, in one example, furfural can be converted to 4-hydroxy-2-cyclopentenone by catalytic hydrogenation. In another example, furfuryl alcohol is obtained in equilibrium with 4-hydroxy-2-cyclopentenone.

Once 4-hydroxy-2-cyclopentenone or a mixture of 4-hydroxy-2-cyclopentenone and furfuryl alcohol is obtained, the product may be converted to cyclopent-2-en-1-one or a mixture of cyclopent-2-en-1-one. The mixture of cyclopent-2-en-1-one includes cyclopent-2-en-1-one and cyclopentanone. The reaction may be performed in the presence of a transition metal catalyst, such as Ni, Cu/Ni, Zn, or combinations thereof and hydrogen, water, or a combination of hydrogen and water to produce cyclopent-2-en-1-one or a mixture containing cyclopent-2-en-1-one. In examples where water is used, water acts as the solvent and source of hydrogen. In some examples, a mixture of cyclopent-2-en-1-one and cyclopentanone may be used in the subsequent step 104.

Figure 3:
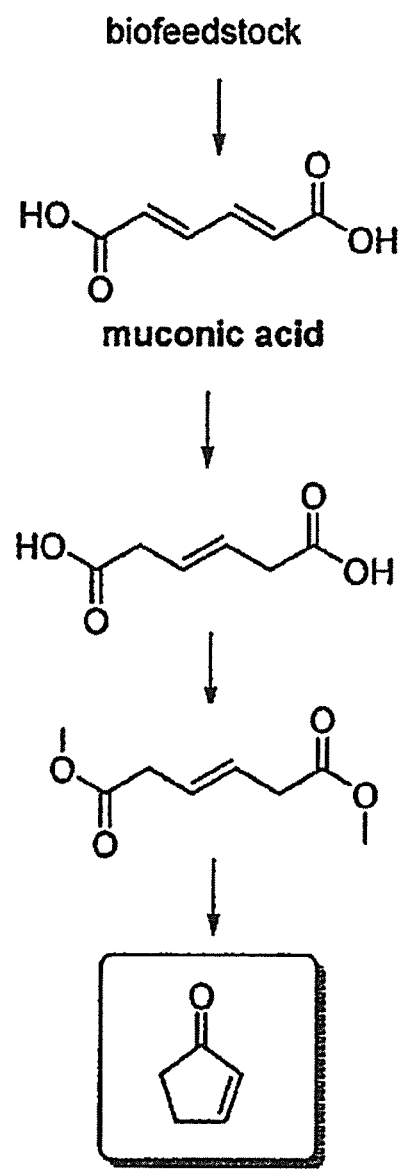
FIG. 3 is another scheme illustrating an example of a method of making cyclopent-2-en-1-one from a biofeedstock.

In another example of step 102, shown in FIG. 3, cyclopent-2-en-1-one is produced from a biofeedstock. Biofeedstocks provide sustainable, abundant sources for the production of cyclopent-2-en-1-one, and subsequently, JP-10 fuel. Any biofeedstock that can be converted to muconic acid may be used. An example of biofeedstock includes lignocellulosic biomass. Any known methods that produce muconic acid from a feedstock may be used. An example includes fermentation of metabolically engineered microorganisms that are genetically engineered to produce muconic acid during fermentation.

After producing muconic acid, a three-step process is employed to produce cyclopent-2-en-1-one. First, the muconic acid is converted to hex-3-enedioic acid. The muconic acid can be converted electrochemically using any known methods. Next, after obtaining hex-3-enedioic acid, the hex-3-enedioic acid may be transesterified with methanol to generate dimethyl-hex-3-en-dioate. Then, dimethyl-hex-3-en-dioate may then be converted to cyclopent-2-en-1-one using a basic catalyst as shown in FIG. 3. Some examples of the basic catalyst used in the reaction include NaOH, KOH, $Na_3PO_4$, $K_3PO_4$.

Figure 4:
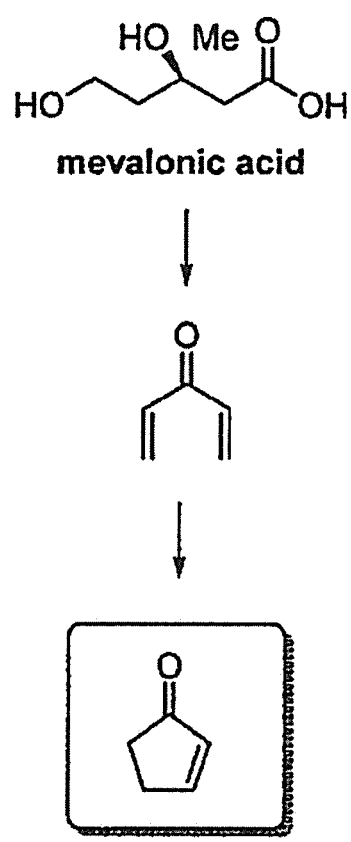
FIG. 4 is another scheme illustrating an example of a method of making cyclopent-2-en-1-one from mevalonic acid.

In yet another example of step 102, shown in FIG. 4, cyclopent-2-en-1-one is produced from mevalonic acid. The mevalonic acid is obtained from a bio-based source. Similar to the other examples, mevalonic acid provides a sustainable, abundant source to produce cyclopent-2-en-1-one, and subsequently, JP-10 fuel. In an example, mevalonic acid may be obtained from metabolically engineered microorganisms via fermentation.

After obtaining mevalonic acid, the mevalonic acid may be converted to cyclopent-2-en-1-one. One specific example includes a two-step process. First, the mevalonic acid is converted to penta-1,4-diene-3-one using known methods. Second, the penta-1,4-diene-3-one may then be cyclized in the presence of a Lewis acid to form cyclopent-2-en-1-one. The Lewis acid used in the cyclization may be any heterogeneous Lewis acid or a Lewis acid in solution. Some examples of heterogeneous Lewis acids include metal oxides, zeolites, aluminosilicates, and combinations thereof. Examples of Lewis acids in solution include $BF_3$, $P_2O_5$, $AlCl_3$, $AlBr_3$, $FeCl_3$, $ZnCl_2$ and combinations thereof.

Figure 5:
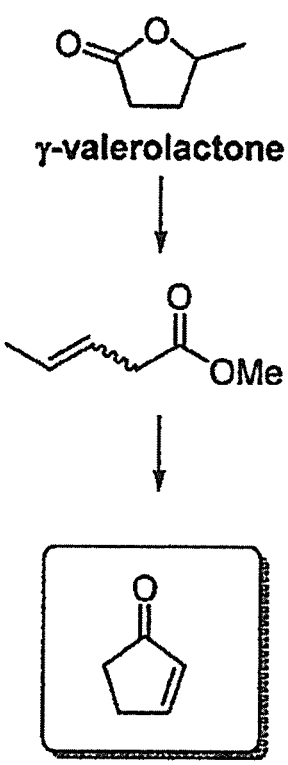
FIG. 5 is another scheme illustrating an example of a method of making cyclopent-2-en-1-one from γ-valerolactone.

In another example of step 102, shown in FIG. 5, cyclopent-2-en-1-one is produced from γ-valerolactone. The γ-valerolactone is obtained from bio-based sources. γ-valerolactone comes from a sustainable, abundant source to produce cyclopent-2-en-1-one, and eventually, JP-10 fuel. An example of the bio-based source is hexoses (e.g., glucose sourced from cellulose or lignocellulose). In an example, hexose is dehydrated to produce levulinic acid. Levulinic acid is then dehydrated to produce γ-valerolactone.

After obtaining γ-valerolactone, an example of producing cyclopent-2-en-1-one includes a two-step process. First, the γ-valerolactone may be converted into methyl-pent-3-enoate. This reaction is conducted with methanol and an acid catalyst. Some examples of the acid catalyst include $H_2SO_4$ or acidic ionic liquids. Second, methyl-pent-3-enoate may then be cyclized in the presence of an acid catalyst to generate cyclopent-2-en-1-one. An example of the acid catalyst includes acidic zeolites.

Referring now to FIG. 1, after forming cyclopent-2-en-1-one or a mixture of cyclopent-2-en-1-one using one of the above examples, step 104 of method 100 includes hydrogenating cyclopent-2-en-1-one or the mixture of cyclopent-2-en-1-one, thereby forming cyclopent-2-en-1-ol or a mixture of cyclopent-2-en-1-ol. An example of step 104 is shown in the first reaction of FIG. 6, which shows the conversion of cyclopent-2-en-1-one to cyclo-2-en-1-ol. When a mixture of cyclopent-2-en-1-ol is formed, the mixture includes cyclopent-2-en-1-ol and cyclopentanol, the latter of which is formed using the first example of step 102 previously described herein. The hydrogenation is conducted at a temperature ranging from about 0° C. to about 30° C. and a pressure ranging from about 1 atm to about 50 atm.

In one example, hydrogenating cyclopent-2-en-1-one or the mixture of cyclopent-2-en-1-one is conducted with borohydride in the presence of a lanthanide(III) catalyst. An example of lanthanide(III) catalyst includes cerium(III) chloride ($CeCl_3 \cdot xH_2O$) and erbium(III) triflate. In another example, the hydrogenation occurs with a ruthenium-based catalyst under a hydrogen atmosphere, where the ruthenium catalyst is bound to one or more ligands. Some examples of the ligand include a bisphosphine ligand, a diamine ligand, or combinations thereof. The hydrogenation with the ruthenium catalysts includes adding two equivalents of a strong base (e.g., KOH) to increase chemoselectivity. In yet another example, an aluminum hydride (e.g., $LiAlH_4$) may be used as a reducing agent to hydrogenate cyclopent-2-en-1-one or the mixture of cyclopent-2-en-1-one. The amount of catalyst or reducing agent varies depending on the catalyst that is used in step 104. In an example, the lanthanide catalyst is present in an amount ranging from about 1 mol % to about 100 mol %. In a specific example, the lanthanide catalyst is present in an amount ranging from about 1 mol % to about 5 mol %. In another example, the ruthenium catalyst is present in an amount ranging from about 0.0001 mol % to about 1 mol %.

After obtaining cyclopent-2-en-1-ol in step 104, step 106 of method 100 includes dehydrating cyclopent-2-en-1-ol or the mixture of cyclopent-2-en-1-ol with a dehydrating agent, thereby forming a cyclopentadiene or a mixture of cyclopentadiene. An example of the reaction is shown in the second reaction of FIG. 6, which shows the conversion of cyclopent-2-en-1-ol to cyclopentadiene. The reaction in step 104 occurs at a temperature ranging from about 20° C. to about 100° C. The reaction in step 104 can be conducted in a liquid or gaseous state, which may vary the reaction time.

Some examples of the dehydrating agent include molecular sieves, an acid catalyst (e.g., AMBERLYST®, NAFION, or aluminum phosphate), a metal salt with high affinity for water e.g., ($MgSO_4$), and combinations thereof. In one example, the cyclopentadiene or the mixture of cyclopentadiene is collected via fractional distillation as the cyclopentaidene or mixture of cyclopentiadiene is formed by conducting the reaction at a temperature greater than the boiling point of cyclopentadiene. In addition, the reaction may be conducted under reduced pressure to enhance the distillation. In some examples, a reduced pressure includes a pressure ranging from about 50 mmHg to about 100 mmHg. In other examples, the reduced pressure includes any pressure lower than atmospheric pressure.

In some examples, the mixture of cyclopentadiene formed in step 106 includes cyclopentadiene trimers, tetramers, heavier oligomers, or a combination thereof in the reaction pot. Heavier oligomers may be any oligomers larger than a tetramer (e.g., pentamer, hexamer, etc.). In other examples, the mixture of cyclopentadiene formed in step 106 includes a mixture of cyclopentadiene trimers, tetramers, cyclopentene, or combinations thereof in the reaction pot. In yet another example, the mixture of cyclopentadiene formed in step 106 includes cyclopentadiene and cyclopentene. When the trimers, tetramers, and heavier oligomers are formed, they can be isolated by adding an organic solvent to the reaction pot followed by either filtration to remove the solid acid catalyst, or washing the organic solution with water to remove water-soluble catalysts. The organic solvent may then be removed under reduced pressure by distillation. Any suitable organic solvent may be used. Some examples include hexanes, diethyl ether, or methylene chloride.

Figure 6:
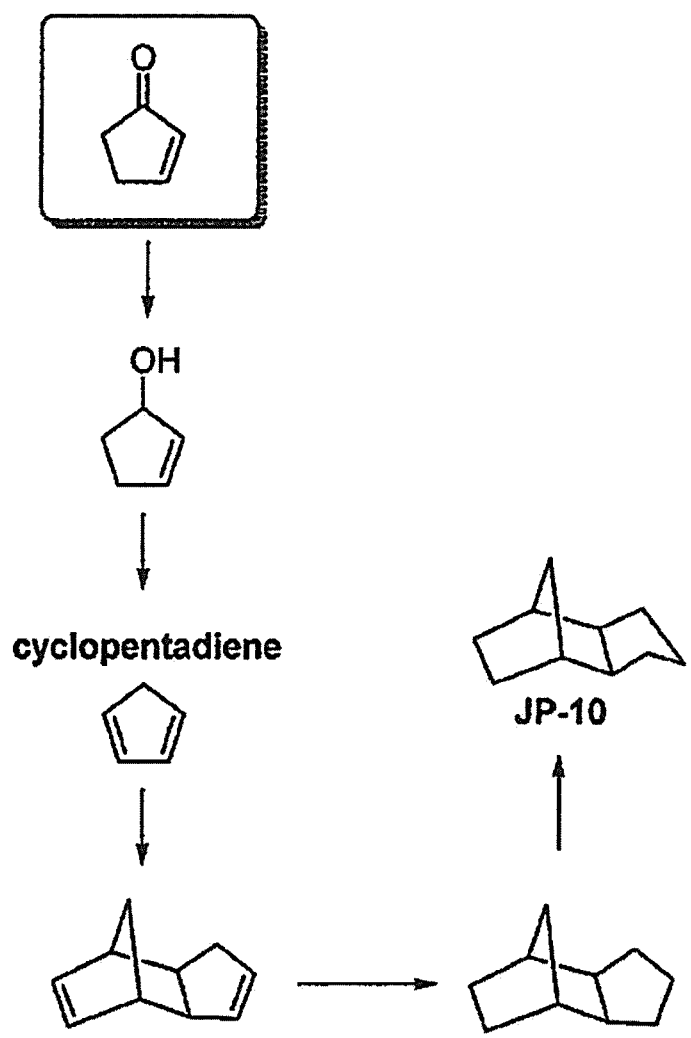
FIG. 6 is a scheme illustrating an example of a method for making exo-tetrahydrodiclyclopentadiene from cyclopent-2-en-1-one.

Referring to FIG. 1, step 108 of method 100 includes converting cyclopentadiene or the mixture of cyclopentadiene to dicyclopentadiene or dihydrodicyclopentadiene. This step occurs via a Diels Alder [4+2] cycloaddition. FIG. 6 shows an example of cyclopentadiene being converted to dicyclopentadiene in the third reaction. The reaction in step 108 occurs at a temperature ranging from about 20° C. to about 100° C. The higher the reaction temperature is, the faster the rate of dimerization occurs. The rate of dimerization may also be increased by using a Lewis acid catalyst. Any suitable Lewis Acid catalyst may be used. Some examples include the Lewis acid catalysts previously mentioned herein in step 102.

In another example of step 108, the method 100 includes converting cyclopentadiene or the mixture of cyclopentadiene to dihydrodicyclopentadiene. In some examples, the mixture of cyclopentadiene may include the cyclopentadiene and the cyclopentene. This reaction also occurs via a Diels Alder [4+2] cycloaddition at a temperature ranging from about 20° C. to about 100° C. as previously disclosed above. However, in this example, dihydrodicyclopentadiene is the product that is formed in step 108.

After producing dicyclopentadiene in step 108, step 110 of method 100 includes hydrogenating dicyclopentadiene or dihydrodicyclopentadiene, thereby forming tetrahydrodicyclopentadiene. An example of step 108 is shown in the fourth reaction in FIG. 6, which shows dicyclopentadiene forming tetrahydrodicyclopentadiene to remove the double bonds. The reaction in step 110 may be performed at a temperature ranging from about 20° C. to about 250° C. and a pressure ranging from about 1 psi to about 3000 psi. In some examples, a transition metal catalyst may be used in the presence of hydrogen gas. Examples of transition metal catalysts include those based on Ni, Pd, Pt, Ru, Rh, Cu, and combinations thereof. In some examples, co-solvents may be used in the reaction. Some examples of co-solvents include any polar solvents, such as methanol, ethanol, isopropanol, acetic acid, or tetrahydrofuran. Regardless of whether step 110 includes hydrogenating dicyclopentadiene or dihydrodicyclopentadiene, the product formed is tetrahydrodicyclopentadiene.

Once tetrahydrodicyclopentadiene is produced, step 112 of the method 100 includes isomerizing tetrahydrodicyclopentadiene, thereby forming exo-tetrahydrodicyclopentadiene. An example of step 112 is shown in FIG. 6 in the final reaction, which shows the isomerization of tetrahydrodicyclopentadiene to exo-tetrahydrodicyclopentadiene. The isomerization may occur with a Lewis acid. Any Lewis acid in solution may be used that isomerizes tetrahydrodicyclopentadiene. For example, any of the Lewis acids in solution previously disclosed herein in step 102 may be used, which includes heterogeneous Lewis acids or Lewis acids in solution. The reaction in step 112 can occur at temperatures ranging from about 20° C. to about 40° C. In some examples, tetrahydrodicyclopentadiene may be isomerized to adamantane. The exo-tetrahydrodicyclopentadiene (JP-10) may be separated from the reaction mixture and distilled to obtain the final product.

To further illustrate the present disclosure, examples are given herein. These examples are provided for illustrative purposes and are not to be construed as limiting the scope of the present disclosure.

EXAMPLES

Example 1: Chemoselective Hydrogenation of Cyclopent-2-Ene-1-One with NaBH

A 500 mL flask was added $CeCl_3 \cdot 7H_2O$ (2.31 g) along with methanol (120 mL). The mixture was stirred until complete dissolution of the salt was observed. The flask was then cooled in an ice bath and cyclopenten-2-ene-1-one (5.00 g) was added to the solution. Solid $NaBH_4$ (2.31 g) was then slowly added in portions over the course of several minutes. The reaction mixture was rigorously stirred for 15 minutes and then quenched by slow addition of 100 mL of deionized water. The mixture was stirred until it became clear, and was then extracted with $Et_2O$. The organic extracts were dried over $MgSO_4$, filtered, and the volatiles were removed under reduced pressure to yield cyclopent-2-ene-1-ol as a colorless oil (98% purity).

Example 2: [Ru]-Catalyzed Chemoselective Hydrogenation of Cyclopent-2-Ene-1-One

A 2-propanol solution of ethylene diamine (1.04 mL, 0.104 mmol) and KOH (1.04 mL, 0.208 mmol) is added to a 6:1 mixture of anhydrous 2-propanol:toluene (20 mL). $RuCl_2[P(C_6H_5)_3]_3$ (0.10 g, 0.104 mmol) is then added to the solution under flowing $N_2$. The resultant mixture is sonicated for 35 minutes. Cyclopent-2-ene-1-one (0.85 g, 10.4 mmol) is added to the mixture, which was then placed in a 100 mL Parr bomb. The bomb is evacuated and refilled with $H_2$ three times and then pressurized to 500 psi and vigorously stirred at room temperature for 24 hours. Upon completion, the reaction mixture is filtered through Celite and concentrated under reduced pressure. The product is then purified by fractional distillation. This reaction can also be conducted with benzene in place of toluene.

Example 3: Chemoselective Hydrogenation of Cyclopent-2-Ene-1-One with $LiAH_4$ (Uncatalyzed)

A 100 mL 3-neck flask under nitrogen was added to a $LiAlH_4$ solution in ether (7.0 mL, 1 M, 7.0 mmol). The solution was heated to reflux and 2-cyclopent-2-ene-1-one (1.18 g, 14.3 mmol) dissolved in 5 mL of ether was added dropwise through an addition funnel. The solution was refluxed for an additional 15 minutes and then allowed to cool to room temperature. This resulted in the precipitation of a significant amount of white solid. The reaction was quenched with small aliquots of water, resulting in the precipitation of additional white solid. The white solid was removed by filtration, washed with additional $Et_2O$, and the filtrate was then dried with $MgSO_4$. Separation of the $MgSO_4$ followed by removal of the volatiles under reduced pressure resulted in a 94% yield of the product. The product consisted of 87% cyclopent-2-ene-1-ol, 9% cyclopentanol, and 4% cyclopentanone.

Example 4: Dehydration of Cyclopent-2-Ene-1-Ol with a Cation Exchange Resin

Cyclopent-2-ene-1-ol (4.0 g, 47.6 mmol) was added to a flask along with Amberlyst-15 (0.4 g). A distillation head and receiving flask were then attached to the flask and the mixture was rapidly stirred and heated to 60° C. under reduced pressure (50-100 torr). The receiving flask was chilled in an acetone/dry ice bath and the product, a mixture of water and cyclopentadiene, was collected in the receiving flask. After the reaction was complete, cyclopentadiene was separated from the frozen water by decantation. The residue, which consisted of a mixture of dicyclopentadiene, tricyclopentadienes, and heavier oligomers, was isolated by dissolution in hexanes, treatment with solid NaHCO$_3$, filtered, and the solvent was removed under reduced pressure. Dicyclopentadiene and tricyclopentadiene were recovered from the residue by fractional distillation.

Example 5: Dehydration of Cyclopent-2-Ene-1-Ol with AlPO$_4$

A reactive distillation apparatus was set up as described in example 4, but Amberlyst-15 was replaced with a mixture of AlPO$_4$ (10 wt %) and MgSO$_4$ (0.1 equivalent). Dicyclopentadiene and tricyclopentadiene were recovered from the residue by fractional distillation.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise stated, any feature described herein can be combined with any aspect or any other feature described herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 0° C. to about 30° C. should be interpreted to include not only the explicitly recited limits of from about 10° C. to about 15° C., but also to include individual values, such as 3° C., 7° C., 13.5° C., etc., and sub-ranges, such as from about 5° C. to about 15° C., etc.

In describing and claiming the examples disclosed herein, the singular forms "a", "an", and "the" include plural referents unless the context clearly dictates otherwise.

What is claimed is:
1. A method for making cyclopentadiene fuel, comprising:
   producing cyclopent-2-en-1-one or a mixture of cyclopent-2-en-1-one from a bio-based sources;
   hydrogenating the cyclopent-2-en-1-one or the mixture of cyclopent-2-en-1-one, thereby forming cyclopent-2-en-1-ol or a mixture of cyclopent-2-en-1-ol;
   dehydrating the cyclopent-2-en-1-ol or the mixture of cyclopent-2-en-1-ol with a dehydrating agent, thereby forming cyclopentadiene or a mixture of cyclopentadiene;
   converting the cyclopentadiene or the mixture of cyclopentadiene to dicyclopentadiene or dihydrodicyclopentadiene;
   hydrogenating the dicyclopentadiene or dihydrodicyclopentadiene, thereby forming tetrahydrodicyclopentadiene; and
   isomerizing the tetrahydrodicyclopentadiene, thereby forming a stream comprising exo-tetrahydrodicyclopentadiene.
2. The method of claim 1, wherein the producing the cyclopent-2-en-1-one from the bio-based sources includes:
   i. obtaining furfural or furfuryl alcohol and converting the furfural or furfuryl alcohol to 4-hydroxy-2-cyclopentenone, or obtaining a combination of furfuryl alcohol and 4-hydroxy-2-cyclopentenone from the bio-based sources; and
   ii. reacting the 4-hydroxy-2-cyclopentenone or the combination of furfuryl alcohol and 4-hydroxy-2-cyclopentenone in the presence of a catalyst and hydrogen, water, or a combination thereof, wherein the catalyst is selected from the group consisting of Ni, Cu/Ni, Zn, and combinations thereof, thereby forming the cyclopent-2-en-1-one or the mixture of cyclopent-2-en-1-one.
3. The method of claim 1, wherein the mixture of cyclopent-2-en-1-one comprises cyclopent-2-en-1-one and cyclopentanone.
4. The method of claim 1, wherein the producing the cyclopent-2-en-1-one from the bio-based sources includes:
   i. obtaining muconic acid from the bio-based sources;
   ii. converting the muconic acid to hex-3-enedioic acid;
   iii. converting the hex-3-enedioic acid to dimethyl-hex-3-en-dioate through transesterification with methanol; and
   iv. converting the dimethyl-hex-3-en-dioate to the cyclopent-2-en-1-one using a basic catalyst.
5. The method of claim 1, wherein the producing the cyclopent-2-en-1-one from the bio-based sources includes:
   i. obtaining penta-1,4-diene-3-one from a bio-based source containing mevalonic acid; and
   ii. cyclizing the penta-1,4-diene-3-one, thereby forming the cyclopent-2-en-1-one.
6. The method of claim 1, wherein the producing the cyclopent-2-en-1-one from the bio-based sources includes:
   i. obtaining gamma-valerolactone from the bio-based sources and converting the gamma-valerolactone to methyl-pent-3-enoate; and
   ii. cyclizing the methyl-pent-3-enoate, thereby forming the cyclopent-2-en-1-one.
7. The method of claim 1, wherein the hydrogenating the cyclopent-2-en-1-one or the mixture of cyclopent-2-en-1- one occurs in the presence of (i) borohydride and a lanthanide (III) catalyst, (ii) an aluminum hydride, or combinations thereof.

8. The method of claim 1, wherein the hydrogenating the cyclopent-2-en-1-one or the mixture of cyclopent-2-en-1-one occurs in the presence of a ruthenium-based catalyst under a hydrogen atmosphere, wherein the ruthenium based catalyst is bound to one or more ligands.

9. The method of claim 1, wherein the dehydrating agent is selected from the group consisting of a molecular sieve, an acid catalyst a metal salt, and combinations thereof.

10. The method of claim 1, wherein the cyclopentadiene or the mixture of cyclopentadiene is collected by reactive distillation as the cyclopentadiene or the mixture of cyclopentadiene is formed.

11. The method of claim 1, wherein the cyclopentadiene or the mixture of cyclopentadiene includes cyclopentadiene trimers, cyclopentadiene tetramers, cyclopentene, or a combination thereof in a reaction vessel.

12. The method of claim 11, wherein the cyclopentadiene trimers and the cyclopentadiene tetramers, the cyclopentene, or the combination thereof are isolated using filtration or washing with water.

13. The method of claim 1, wherein the converting the cyclopentadiene or the mixture of cyclopentadiene to dicyclopentadiene occurs using heat, a Lewis acid catalyst, or a combination thereof.

14. The method of claim 1, wherein the hydrogenating the dicyclopentadiene is performed using a transition metal catalyst based on a metal selected from the group consisting of Ni, Pd, Pt, Ru, Rh, Cu, and combinations thereof.

15. The method of claim 1, wherein the hydrogenating the dicyclopentadiene is performed at a temperature ranging from about 20° C. to about 250° C. and a pressure ranging from about 1 psi to about 3000 psi.

16. The method of claim 1, wherein the isomerizing the tetrahydrodicyclopentadiene occurs by a reaction with a Lewis acid catalyst selected from the group consisting of $BF_3$, $P_2O_5$, $AlCl_3$, $AlBr_3$, $FeCl_3$, $ZnCl_2$, and combinations thereof.

17. The method of claim 1, wherein the exo-tetrahydrodicyclopentadiene is isomerized to adamantane.

18. The method of claim 1, wherein the exo-tetrahydrodicyclopentadiene is isolated by separating and distilling the stream comprising exo-tetrahydrodicyclopentadiene.

\* \* \* \* \*